(12) United States Patent
Wang et al.

(10) Patent No.: US 8,067,650 B2
(45) Date of Patent: *Nov. 29, 2011

(54) PROCESS FOR THE PRODUCTION OF HFO TRANS-1234ZE FROM HFC-245FA

(75) Inventors: Haiyou Wang, Williamsville, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/775,318

(22) Filed: Jul. 10, 2007

(65) Prior Publication Data

US 2008/0051611 A1 Feb. 28, 2008

Related U.S. Application Data

(60) Provisional application No. 60/839,873, filed on Aug. 24, 2006.

(51) Int. Cl.
*C07C 17/00* (2006.01)
(52) U.S. Cl. ........................ 570/236; 570/156
(58) Field of Classification Search .................. 570/156, 570/236
See application file for complete search history.

(56) References Cited

U.S. PATENT DOCUMENTS

| | | | | |
|---|---|---|---|---|
| 3,398,204 A | * | 8/1968 | Gallant | 570/236 |
| 5,895,825 A | * | 4/1999 | Elsheikh et al. | 570/167 |
| 5,986,151 A | * | 11/1999 | Van Der Puy | 570/175 |
| 6,124,510 A | * | 9/2000 | Elsheikh et al. | 570/156 |
| 6,548,719 B1 | | 4/2003 | Nair et al. | 570/157 |
| 2005/0090698 A1 | | 4/2005 | Merkel et al. | 570/155 |

FOREIGN PATENT DOCUMENTS

| | | |
|---|---|---|
| EP | 0939071 A | 9/1999 |
| EP | 974571 | 1/2000 |
| EP | 1900716 A | 3/2008 |
| JP | 11-140002 | 5/1999 |
| WO | 2007019355 A | 2/2007 |

* cited by examiner

*Primary Examiner* — Sudhakar Katakam
(74) *Attorney, Agent, or Firm* — Bruce O. Bradford

(57) ABSTRACT

This invention relates a process for the manufacture of the HFO trans-1,3,3,3-tetrafluoropropene (HFO trans-1234ze). More particularly, the invention pertains to a process for the manufacture of the HFO trans-1234ze by first dehydrofluorinating 1,1,1,3,3-pentafluoropropane to thereby produce a mixture of cis-1,3,3,3-tetrafluoropropene, trans-1,3,3,3-tetrafluoropropene and hydrogen fluoride. Then optionally recovering hydrogen fluoride and then recovering trans-1,3,3,3-tetrafluoropropene.

9 Claims, 1 Drawing Sheet

PROCESS FOR THE PRODUCTION OF HFO TRANS-1234ZE FROM HFC-245FA

CROSS REFERENCE TO RELATED APPLICATION

This application claims the benefit of co-pending U.S. provisional patent application Ser. No. 60/839,873 filed Aug. 24, 2006, which is incorporated herein by reference.

BACKGROUND OF THE INVENTION

This invention relates a process for the manufacture of trans-1,3,3,3-tetrafluoropropene (HFO trans-1234ze). More particularly, the invention pertains to a process for the manufacture of the HFO trans-1234ze by first dehydrofluorinating 1,1,1,3,3-pentafluoropropane to thereby produce a mixture of cis-1,3,3,3-tetrafluoropropene, trans-1,3,3,3-tetrafluoropropene and hydrogen fluoride. Then optionally recovering hydrogen fluoride, followed by recovering trans-1,3,3,3-tetrafluoropropene.

Traditionally, chlorofluorocarbons (CFCs) like trichlorofluoromethane and dichlorodifluoromethane have been used as refrigerants, blowing agents and diluents for gaseous sterilization. In recent years, there has been widespread concern that certain chlorofluorocarbons might be detrimental to the Earth's ozone layer. As a result, there is a worldwide effort to use halocarbons which contain fewer or no chlorine substituents. Accordingly, the production of hydrofluorocarbons, or compounds containing only carbon, hydrogen and fluorine, has been the subject of increasing interest to provide environmentally desirable products for use as solvents, blowing agents, refrigerants, cleaning agents, aerosol propellants, heat transfer media, dielectrics, fire extinguishing compositions and power cycle working fluids. In this regard, trans-1,3,3,3-tetrafluoropropene (trans-1234ze) is a compound that has the potential to be used as a zero Ozone Depletion Potential (ODP) and a low Global Warming Potential (GWP) refrigerant, blowing agent, aerosol propellant, solvent, etc, and also as a fluorinated monomer.

It is known in the art to produce HFO-1234ze (i.e. HydroFluoroOlefin-1234ze). For example, U.S. Pat. No. 5,710,352 teaches the fluorination of 1,1,1,3,3-pentachloropropane (HCC-240fa) to form HCFC-1233zd and a small amount of HFO-1234ze. U.S. Pat. No. 5,895,825 teaches the fluorination of HCFC-1233zd to form HFC-1234ze. U.S. Pat. No. 6,472,573 also teaches the fluorination of HCFC-1233zd to form HFO-1234ze. U.S. Pat. No. 6,124,510 teaches the formation of cis and trans isomers of HFO-1234ze by the dehydrofluorination of HFC-245fa in the presence of an oxygen-containing gas using either a strong base or a chromium-based catalyst. European patent EP 0939071 describes the formation of HFC-245fa via the fluorination of HCC-240fa through intermediate reaction product which is an azeotropic mixture of HCFC-1233zd and HFO-1234ze.

It has been determined that these known processes are not economical relative to their product yield. It has also been noted that significant amount of cis-1234ze is generated together with its trans-isomer in these know processes. Hence, there is a need for means by which trans-1234ze can be isolated from product mixtures and cis-1234ze can be recycled. Accordingly, the present invention provides an integrated process for producing trans-1234ze from which highly pure trans-1234ze can be obtained at a higher yield than prior art processes and cis-1234ze can be recycled in contrast to known processes. In particular, it has now been found that trans-1234ze may be formed by dehydrofluorinating 1,1,1,3,3-pentafluoropropane in the absence of an oxygen-containing gas to produce a mixture of cis-1,3,3,3-tetrafluoropropene, trans-1,3,3,3-tetrafluoropropene and hydrogen fluoride. Then optionally, but preferably recovering hydrogen fluoride and then recovering trans-1,3,3,3-tetrafluoropropene. The cis-1234ze and HFC-245fa may then be recycled.

DESCRIPTION OF THE INVENTION

Figure 1:
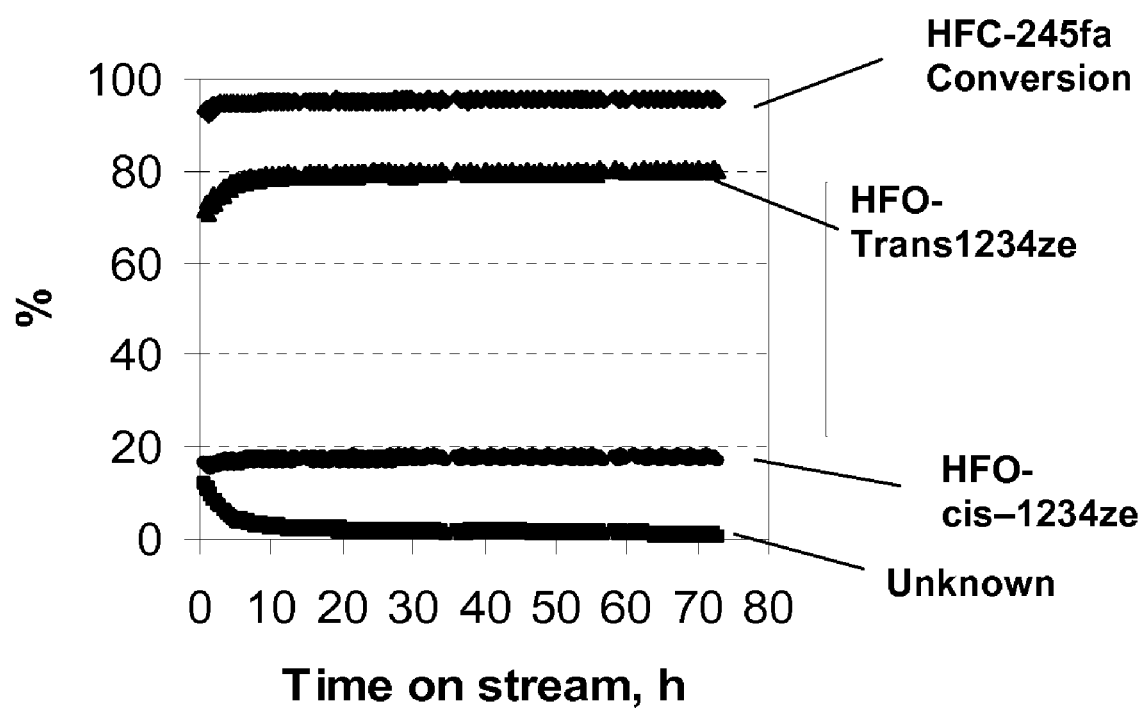
FIG. 1 is a graph showing the effect of time on stream on the performance of Florinated Chromia Catalyst" (Reaction conditions: 20 cc catalyst, 12 g/h HFC-245fa, 350° C., 1 atmosphere) from Example 1.

The invention provides a process for the production of trans-1,3,3,3-tetrafluoropropene which comprises:
(a) dehydrofluorinating 1,1,1,3,3-pentafluoropropane to thereby produce a result comprising cis-1,3,3,3-tetrafluoropropene, trans-1,3,3,3-tetrafluoropropene and hydrogen fluoride;
(b) optionally recovering hydrogen fluoride from the result of step (a); and
(c) recovering trans-1,3,3,3-tetrafluoropropene.

The invention also provides a continuous, integrated manufacturing process for the production of trans-1,3,3,3-tetrafluoropropene which comprises:
(a) dehydrofluorinating 1,1,1,3,3-pentafluoropropane in a vapor phase reaction to thereby produce a result comprising cis-1,3,3,3-tetrafluoropropene, trans-1,3,3,3-tetrafluoropropene and hydrogen fluoride;
(b) recovering hydrogen fluoride from the result of step (a); and
(c) recovering trans-1,3,3,3-tetrafluoropropene.

The first step of the process involves the catalytic conversion of HFC-245fa by dehydrofluorinating HFC-245fa to produce a result comprising a combination of cis-1,3,3,3-tetrafluoropropene, trans-1,3,3,3-tetrafluoropropene and hydrogen fluoride. Dehydrofluorination reactions are well known in the art. Preferably dehydrofluorination of HFC-245fa is done in a vapor phase, and more preferably in a fixed-bed reactor in the vapor phase. The dehydrofluorination reaction may be conducted in any suitable reaction vessel or reactor, but it should preferably be constructed from materials which are resistant to the corrosive effects of hydrogen fluoride such as nickel and its alloys, including Hastelloy, Inconel, Incoloy, and Monel or vessels lined with fluoropolymers. These may be single or multiple tubes packed with a dehydrofluorinating catalyst which may be one or more of fluorinated metal oxides in bulk form or supported, metal halides in bulk form or supported, and carbon supported transition metals, metal oxides and halides. Suitable catalysts non-exclusively include fluorinated chromia (fluorinated $Cr_2O_3$), fluorinated alumina (fluorinated $Al_2O_3$), metal fluorides (e.g., $CrF_3$, $AlF_3$) and carbon supported transition metals (zero oxidation state) such as Fe/C, Co/C, Ni/C, Pd/C or transition metals halides. The HFC-245fa is introduced into the reactor either in pure form, impure form, or together with an optional inert gas diluent such as nitrogen, argon, or the like. In a preferred embodiment of the invention, the HFC-245fa is pre-vaporized or preheated prior to entering the reactor. Alternately, the HFC-245fa is vaporized inside the reactor. Useful reaction temperatures may range from about 100° C. to about 600° C. Preferred temperatures may range from about 150° C. to about 450° C., and more preferred temperatures may range from about 200° C. to about 350° C. The reaction may be conducted at atmospheric pressure, super-atmospheric pressure or under vacuum. The vacuum pressure can be from about 5 torr to about 760 torr. Contact time of the HFC-245fa with the catalyst may range from about 0.5 seconds to about 120 seconds, however, longer or shorter times can be used.

In the preferred embodiment, the process flow is in the down or up direction through a bed of the catalyst. It may also be advantageous to periodically regenerate the catalyst after prolonged use while in place in the reactor. Regeneration of the catalyst may be accomplished by any means known in the art, for example, by passing air or air diluted with nitrogen over the catalyst at temperatures of from about 100° C. to about 400° C., preferably from about 200° C. to about 375° C., for from about 0.5 hour to about 3 days. This is followed by either HF treatment at temperatures of from about 25° C. to about 400° C., preferably from about 200° C. to about 350° C. for fluorinated metal oxide catalysts and metal fluoride ones or $H_2$ treatment at temperatures of from about 100° C. to about 400° C., preferably from about 200° C. to about 350° C. for carbon supported transition metal catalysts.

In an alternate embodiment of the invention, dehydrofluorination of HFC-245fa can also be accomplished by reacting it with a strong caustic solution that includes, but is not limited to KOH, NaOH, $Ca(OH)_2$ and CaO at an elevated temperature. In this case, the caustic strength of the caustic solution is of from about 2 wt % to about 100 wt %, more preferably from about 5 wt % to about 90 wt % and most preferably from about 10 wt % to about 80 wt %. The reaction may be conducted at a temperature of from about 20° C. to about 100° C., more preferably from about 30° C. to about 90° C. and most preferably from about 40° C. to about 80° C. As above, the reaction may be conducted at atmospheric pressure, super-atmospheric pressure or under vacuum. The vacuum pressure can be from about 5 torr to about 760 torr. In addition, a solvent may optionally be used to help dissolve the organic compounds in the caustic solution. This optional step may be conducted using solvents that are well known in the art for said purpose.

Optionally but preferably, hydrogen fluoride is then recovered from the result of the dehydrofluorination reaction. Recovering of hydrogen fluoride is conducted by passing the composition resulting from the dehydrofluorination reaction through a sulfuric acid extractor to remove hydrogen fluoride, subsequently desorbing the extracted hydrogen fluoride from the sulfuric acid, and then distilling the desorbed hydrogen fluoride. The separation may be conducted by adding sulfuric acid to the mixture while the mixture is in either the liquid or gaseous states. The usual weight ratio of sulfuric acid to hydrogen fluoride ranges from about 0.1:1 to about 100:1. One may begin with a liquid mixture of the fluorocarbons and hydrogen fluoride and then add sulfuric acid to the mixture.

The amount of sulfuric acid needed for the separation depends on the amount of HF present in the system. From the solubility of HF in 100% sulfuric acid as a function of a temperature curve, the minimum practical amount of sulfuric acid can be determined. For example at 30° C. about 34 g of HF will dissolve in 100 g of 100% sulfuric acid. However, at 100° C. only about 10 g of HF will dissolve in the 100% sulfuric acid. Preferably the sulfuric acid used in this invention has a purity of from about 50% to 100%.

In the preferred embodiment, the weight ratio of sulfuric acid to hydrogen fluoride ranges from about 0.1:1 to about 1000:1. More preferably the weight ratio ranges from about 1:1 to about 100:1 and most preferably from about 2:1 to about 50:1. Preferably the reaction is conducted at a temperature of from about 0° C. to about 100° C., more preferably from about 0° C. to about 40° C., and most preferably from about 20° C. to about 40° C. The extraction is usually conducted at normal atmospheric pressure, however, higher or lower pressure conditions may be used by those skilled in the art. Upon adding the sulfuric acid to the mixture of fluorocarbons and HF, two phases rapidly form. An upper phase is formed which is rich in the fluorocarbons and a lower phase which is rich in HF/sulfuric to acid. By the term "rich" is meant, the phase contains more than 50% of the indicated component in that phase, and preferably more than 80% of the indicated component in that phase. The extraction efficiency of the fluorocarbon can range from about 90% to about 99%.

After the separation of the phases, one removes the upper phase rich in the fluorocarbons from the lower phase rich in the hydrogen fluoride and sulfuric acid. This may be done by decanting, siphoning, distillation or other techniques well known in the art. One may optionally repeat the fluorocarbon extraction by adding more sulfuric acid to the removed lower phase. With about a 2.25:1 weight ratio of sulfuric acid to hydrogen fluoride, one can obtain an extraction efficiency of about 92% in one step. Preferably one thereafter separates the hydrogen fluoride and sulfuric acid. One can take advantage of the low solubility of HF in sulfuric at high temperatures to recover the HF from sulfuric. For example, at 140° C., only 4 g of HF will dissolve in 100% sulfuric acid. One can heat the HF/sulfuric acid solution up to 250° C. to recover the HF. The HF and sulfuric acid may then be recycled. That is, the HF may be recycled to a preceding reaction for the formation of the HFC-245fa and the sulfuric acid may be recycled for use in further extraction steps.

In another embodiment of the invention, the recovering of hydrogen fluoride from the mixture of fluorocarbon and hydrogen fluoride may be conducted in a gaseous phase by a continuous process of introducing a stream of sulfuric acid to a stream of fluorocarbon and hydrogen fluoride. This may be conducted in a standard scrubbing tower by flowing a stream of sulfuric acid countercurrent to a stream of fluorocarbon and hydrogen fluoride. Sulfuric acid extraction is described, for example in U.S. Pat. No. 5,895,639, which is incorporated herein by reference. In another embodiment, removing hydrogen fluoride from the result of dehydrofluorination is conducted by passing that result through a scrubber comprising water and a caustic, followed by drying such as in a sulfuric acid drying column.

Alternatively, HF can be recovered or removed by using water or caustic scrubbers, or by contacting with a metal salt. When water extractor is used, the technique is similar to that of sulfuric acid. When caustic is used, HF is just removed from system as a fluoride salt in aqueous solution. When metal salt (e.g. potassium fluoride, or sodium fluoride) is used, it can be used neat or in conjunction with water. HF can be recovered when metal salt is used.

Thereafter, trans-1,3,3,3-tetrafluoropropene may be recovered from the reaction product mixture comprised of unreacted starting materials and by-products, including cis-1,3,3, 3-tetrafluoropropene and any by-products and/or starting materials by any means known in the art, such as by extraction and preferably distillation. The mixture of trans-1,3,3,3-tetrafluoropropene, cis-1,3,3,3-tetrafluoropropene, unreacted HFC-245fa and any by-products and are passed through a distillation column. For example, the distillation may be preferably conducted in a standard distillation column at atmospheric pressure, super-atmospheric pressure or a vacuum. Preferably the pressure is less than about 300 psig, preferably less than about 150 psig and most preferably less than 100 psig. The pressure of the distillation column inherently determines the distillation operating temperature. Trans-1,3,3,3-tetrafluoropropene has a boiling point of about −19° C.; cis-1,3,3,3-tetrafluoropropene has a boiling point of about 9° C.; HFC-245fa has a boiling point of about 15° C. Trans-1,3,3,3-tetrafluoropropene may be recovered as distillate by operating the distillation column at from about −10° C. to about 90° C., preferably from about 0° C. to about 80° C. Single or multiple distillation columns may be used. The distillate portion includes substantially all the trans-1,3,3,3-tetrafluoropropene. The bottom stream of the distillation includes cis-1,3,3,3-tetrafluoropropene, HFC-245fa, a small amount of unrecovered HF and as well as any other impurities. In the preferred embodiment, part of the HFC-245fa is recycled back for subsequent dehydrofluorinating reactions, the cis-1,3,3,3-tetrafluoropropene and/or mixture of cis-1,3,3,3-tetrafluoropropene and 245fa is subjected to a fluorination reaction to HFC-245fa for recycle to step (a). The recovered HF from step (b) and any HF present in the bottoms of the distillation may also be recovered and recycled back for subsequent fluorination reactions.

Fluorination of the cis-1,3,3,3-tetrafluoropropene to HFC-245fa may be conducted in a liquid phase or a vapor phase. Vapor phase fluorination of cis-1,3,3,3-tetrafluoropropene to HFC-245fa may be done by reacting cis-1,3,3,3-tetrafluoropropene with HF in the presence of a catalyst in a reaction vessel. The fluorination reaction may be conducted in any suitable fluorination reaction vessel or reactor but it should preferably be constructed from materials which are resistant to the corrosive effects of hydrogen fluoride such as nickel and its alloys, including Hastelloy, Inconel, Incoloy, and Monel or vessels lined with fluoropolymers.

Preferred vapor phase fluorination catalysts include, but are not limited to, transition metal halides, Group IVb and Vb metal halides, and combinations thereof, preferably supported on activated carbon or fluorinated alumina. More specifically, preferred fluorination catalysts non-exclusively include $SbCl_5$, $SbCl_3$, $TaCl_5$, $SnCl_4$, $NbCl_5$, $TiCl_4$, $MoCl_5$, $Cr_2O_3$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof, where it is understood that after pre-treatment with HF or during reaction in the presence of HF the above mentioned catalyst will be partially fluorinated. For catalyst supported on carbon, the preferred catalysts are $SbCl_3$ and $SbCl_5$ halides supported on activated carbon. Fluorination catalysts having a purity of at least 90% are preferred. The fluorination catalyst is present in an amount sufficient to drive the reaction.

Any water in the hydrogen fluoride (HF) will react with and deactivate the fluorination catalyst. Therefore substantially anhydrous hydrogen fluoride is preferred. By "substantially anhydrous" it is meant that the HF contains less than about 0.05 weight % water and preferably contains less than about 0.02 weight % water. However, one of ordinary skill in the art will appreciate that the presence of water in the HF can be compensated for by increasing the amount of catalyst used.

The vapor phase fluorination reaction may be conducted at a temperature of from about 50° C. to about 400° C., preferably from about 60° C. to about 375° C. and more preferably from about 65° C. and 350° C. The fluorination may be conducted at a pressure of from about 15 psia to about 215 psia, more preferably from about 15 psia to about 165 psia and most preferably from about 30 psia to about 100 psia. In the process of the invention, the reactor is preferably preheated to the desired fluorination reaction temperature while anhydrous HF is fed to the reactor. The cis-1,3,3,3-tetrafluoropropene and HF may be fed to the reactor at the desired temperatures and pressures that are described herein. In a preferred embodiment of the invention, either or both of the cis-1,3,3,3-tetrafluoropropene and HF are pre-vaporized or preheated prior to entering the reactor. Alternately, the cis-1,3,3,3-tetrafluoropropene and HF are vaporized inside the reactor. During the fluorination reaction, cis-1,3,3,3-tetrafluoropropene and HF are reacted in a vapor phase with the fluorination catalyst. The reactant vapor is allowed to contact the fluorination catalyst for from about 0.01 to about 240 seconds, more preferably from about 0.1 to about 60 seconds and most preferably from about 0.5 to about 20 seconds.

In the preferred embodiment, the process flow is in the down direction through a bed of the catalyst. Before each use, the catalyst is preferably dried, pre-treated and activated. It may also be advantageous to periodically regenerate the catalyst after prolonged use while in place in the reactor. For $Cr_2O_3$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ catalysts, pre-treatment can be done by heating the catalyst to about 150° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art, for example, by passing air or air diluted with nitrogen over the catalyst at temperatures of from about 100° C. to about 400° C., preferably from about 200° C. to about 375° C., for from about 1 hour to about 3 days, depending on the size of the reactor. For $SbCl_5$, $SbCl_3$, $TaCl_5$, $SnCl_4$, $NbCl_5$, $TlCl_4$, $MoCl_5$ catalysts, supported on a solid support such as activated carbon, pre-treatment or activation can be done by first heating the catalyst to about 30° C. to 250° C. in a stream of nitrogen or other inert gas. It is then treated with a stream of HF in the absence or presence of an oxidizing agent such as chlorine gas in order to obtain high catalyst activity. In addition, the catalyst may optionally be kept active by co-feeding chlorine to the reactor during reaction.

HFC-245fa may be recovered from the fluorination reaction product mixture comprised of unreacted starting materials and by-products by any means known in the art, such as described in U.S. Pat. No. 5,763,706. In the preferred embodiment, any HF present may also be recovered and recycled back for subsequent fluorination reactions.

Alternatively, a liquid phase process may be used to fluorinate cis-1234ze to HFC-245fa. Cis-1234ze is reacted with HF in the presence of a liquid phase fluorination catalyst. HFC-245fa is then recovered. Starting materials and by-products can be recycled. A liquid phase fluorination catalyst is charged to a fluorination reactor prior to heating of the reactor. Useful fluorination catalysts non-exclusively include transition metal halides, Groups IVa and Va, metal halides, Group IVb metal halides, Group Vb metal halides and Group VIb metal halides and mixtures thereof. Such non-exclusively include $SbCl_5$, $SbCl_3$, $TaCl_5$, $SnCl_4$, $NbCl_5$, $TiCl_4$, $MoCl_5$ and mixtures thereof. The reactor according to this invention may be any suitable fluorination reaction vessel such as those described above.

Cis-1234ze or mixture of cis-1234ze and HFC-245fa and HF are simultaneously fed to the reactor after the reactor reaches the desired temperature. The reactor is run at a preferred temperature ranging from about 60° C. to about 140° C.; more preferably from about 70° C. to about 120.° C. and most preferably from about 80° C. to about 110° C. The HF to Cis-1234ze mole ratio preferably ranges from about 4 to about 10; more preferably from about 5 to about 9 and most preferably from about 5.5 to about 8. Reactor pressure is preferably maintained at from about 0 to about 300 psig; more preferably from about 50 to about 275 psig and most preferably from about 100 to about 260 psig. A chlorine feed is optional, but preferred to keep the catalyst active. A chlorine feed is especially advantageous when antimony chloride is used as catalyst. For every pound of $SbCl_5$ catalyst, about 0.06 to about 0.2 lb. of chlorine is fed to the reactor. Chlorine can be charged in either a batch or continuous mode.

Optionally, but preferably, a top catalyst stripper is used such that most of the unreacted HF and catalyst is refluxed back to the reactor. The catalyst stripper is a packed pipe equipped with a condenser and this step is conducted by adjusting the temperature of the condenser to a range of from about 20° C. to about 100° C. The HFC-245fa is recovered such as described in U.S. Pat. No. 5,763,706.

The following non-limiting examples serve to illustrate the invention.

Example 1

HRC-245fa Dehydrofluorinaton Over Fluorinated $Cr_2O_3$ Catalyst

The catalyst used in this example was 20 cc of fluorined chromia catalyst (fluorinated $Cr_2O_3$). A >99% pure HFC-245fa feed was passed over this catalyst at a rate of 12 g/h at a temperature which ranged from 250° C. to 350° C. As shown in Table 1, with increasing reaction temperature from 250° C. to 350° C., the HFC-245fa conversion was increased from 65.2 to 96.0%, while the selectivity to trans-1234ze was slightly decreased from 84.7 to 80.6%. At 250° C., trans/cis-1234ze appeared to be the only products. As shown in FIG. 1, at 350° C., after an activation period of about 8 hours, the conversion of HFC-245fa and the selectivity to trans-1234ze remained at the same levels during the period of the study which lasted for 72 hours. These results indicate that the fluorinated $Cr_2O_3$ catalyst is very active and selective for converting 245fa to cis-1234ze and trans-1234ze and the catalyst has very high stability.

TABLE 1

Effect of reaction temperature on the performance of "Fluorinated Chromia Catalyst" during HFC-245fa dehydrofluorination

| Temp. (° C.) | HFC-245fa conversion, % | trans-1234ze selectivity % | cis-1234ze selectivity % | unknown selectivity % | trans-1234ze lbs./hr./ft³ |
|---|---|---|---|---|---|
| 350 | 96.0 | 80.6 | 18.0 | 1.4 | 26.0 |
| 300 | 90.2 | 83.0 | 16.8 | 0.2 | 25.1 |
| 275 | 81.5 | 83.9 | 16.0 | 0.1 | 23.0 |
| 250 | 65.2 | 84.7 | 15.3 | 0.0 | 18.5 |

Reaction conditions: 20 cc catalyst, 12 g/h HFC-245fa, 1 atm.

Example 2

HFC-245fa Dehydrofluorinaton Over Metal Fluoride Catalysts

The catalysts used in this example include three metal fluoride catalysts, namely, $AlF_3$, $FeF_3$, and 10% $MgF_2$–90% $AlF_3$. 20 cc of each catalyst was used during reaction. A >99% pure HFC-245fa feed was passed over each of the three catalysts at a rate of 12 g/hour at 350° C. As shown in Table 2, both $AlF_3$ and 10% $MgF_2$–90% $AlF_3$ provided high activity (>95% HFC-245fa conversion) for HFC-245 dehydrofluorination, while $FeF_3$ exhibited much lower activity (<60% HFC-245fa conversion). The selectivity to HFO-trans-1234ze over the $AlF_3$ and 10% $MgF_2$–90% $AlF_3$ catalysts was about 80% at 350° C.

TABLE 2

HFC-245fa dehydrofluorination over metal fluoride catalysts

| Catalyst | HFC-245fa Conversion % | trans-1234ze selectivity % | cis-1234ze selectivity % | unknown selectivity % | trans-1234ze lbs/hr/ft3 |
|---|---|---|---|---|---|
| $AlF_3$ | 96.8 | 80.4 | 16.3 | 3.3 | 26.2 |
| $FeF_3$ | 55.4 | 78.3 | 21.1 | 0.6 | 14.6 |
| 10% $MgF_2$—90% $AlF_3$ | 98.3 | 78.6 | 17.5 | 4.0 | 26.0 |

Reaction conditions: 20 cc catalyst, 12 g/h HFC-245fa, 350° C., 1 atm

Example 3

HFC-245fa Dehydrofluorinaton Over Activated Carbon Supported Metal Catalysts

The catalysts used in Example 3 include three activated carbon supported metal catalysts, namely, 0.5 wt % Fe/AC, 0.5 wt % Ni/AC, and 5.0 wt % Co/AC. 20 cc of each catalyst was used during reaction. A >99% pure HFC-245fa feed was passed over each of the three catalysts at a rate of 12 g/h at 350° C. As shown in Table 3, among the activated carbon supported non-precious metal catalysts, iron exhibited the highest activity. At a reaction temperature of 525° C. the 0.5 wt % Fe/AC catalyst provided a cis/trans-1234ze selectivity of about 91% and a HFC-245fa conversion of about 80%.

TABLE 3

HFC-245fa dehydrofluorination over activated carbon supported metal catalysts at 525° C.

| Catalyst | HFC-245fa Conversion % | trans-1234ze selectivity % | cis-1234ze selectivity % | unknown selectivity % | trans-1234ze lbs/hr/ft3 |
|---|---|---|---|---|---|
| 0.5 wt % Fe/AC | 80.0 | 67.8 | 23.4 | 8.8 | 18.2 |
| 0.5 wt % Ni/AC | 24.8 | 46.6 | 16.6 | 36.8 | 3.9 |
| 5.0 wt % Co/AC | 10.9 | 20.1 | 7.2 | 72.7 | 0.7 |

Reaction conditions: 20 cc catalyst, 12 g/h HFC-245fa, 525° C., 1 atm

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A continuous integrated manufacturing process for the production of trans-1,3,3,3-tetrafluoropropene which consists of the steps:
   (a) dehydrofluorinating 1,1,1,3,3-pentafluoropropane in a vapor phase reaction, in the absence of an oxygen-containing gas, to produce a product stream comprising cis-1,3,3,3-tetrafluoropropene, trans-1,3,3,3-tetrafluoropropene and hydrogen fluoride;
   (b) removing the hydrogen fluoride from the product stream of step (a); and
   (c) recovering trans-1,3,3,3-tetrafluoropropene from the product stream of step (a) or step (b) by distilling the product stream of step (a) or step (b) to isolate and recover the trans-1,3,3,3-tetrafluoropropene therefrom.

2. The process of claim 1, further comprising the steps;
   (d) recovering a residue from step (c) comprising one or more of hydrogen fluoride, cis-1,3,3,3-tetrafluoropropene and 1,1,1,3,3-pentafluoropropane;
   (e) individually isolating and recovering the hydrogen fluoride, cis-1,3,3,3-tetrafluoro-propene and 1,1,1,3,3-pentafluoropropane from the residue in step (d); and
   (f) isolating and recovering at least one of the cis-1,3,3,3-tetrafluoropropene and 1,1,1,3,3-pentafluoropropane from the residue in step (e) and recycling the recovered material back to step (a).

3. The process of claim 2, further comprising the step of recovering cis-1,3,3,3-tetrafluoropropene or a mixture of cis-1,3,3,3-tetrafluoropropene and 1,1,1,3,3-pentafluoropropane from the residue and converting cis-1,3,3,3-tetrafluoropropene to 1,1,1,3,3-pentafluoropropane by fluorination.

4. The process of claim 3, wherein the fluorination reaction is a liquid phase reaction.

5. The process of claim 3, wherein the fluorination reaction is a vapor phase reaction.

6. The process of claim 3, wherein the resulting 1,1,1,3,3-pentafluoropropane is recycled back to step (a).

7. The process of claim 1, wherein the dehydrofluorinating is conducted with a catalyst comprising one or more of fluorinated $Cr_2O_3$, $AlF_3$, $FeF_3$, 10% $MgF_2$-90% $AlF_3$, Fe on activated carbon, Ni on activated carbon, and Co on activated carbon.

8. The process of claim 7, wherein the dehydrofluorinating is conducted in a vapor phase at a temperature of from about 100° C. to about 600° C.; at a contact time of the 1,1,1,3,3-pentafluoropropane with the catalyst of from about 0.5 seconds to about 120 seconds.

9. The process of claim 1, wherein step (b) further comprises the recovering of the hydrogen fluoride by passing the product stream of step (a) through a sulfuric acid extractor, desorbing the extracted hydrogen fluoride from the sulfuric acid, and then distilling the desorbed hydrogen fluoride.

* * * * *